United States Patent [19]

Timm et al.

[11] Patent Number: 4,881,531

[45] Date of Patent: Nov. 21, 1989

[54] POSITION STABLE SEGMENTED COLUMN PENILE PROSTHESIS

[75] Inventors: Gerald W. Timm, Woodland; Stephen K. Sundquist, Chanhassen, both of Minn.

[73] Assignee: Dacomed Corporation, Minneapolis, Minn.

[21] Appl. No.: 346,386

[22] Filed: Apr. 27, 1989

Related U.S. Application Data

[63] Continuation of Ser. No. 934,245, Nov. 21, 1986, abandoned.

[51] Int. Cl.$^4$ .............................................. A61F 2/26
[52] U.S. Cl. ......................................................... 128/79
[58] Field of Search ............................................. 128/79

[56] References Cited

U.S. PATENT DOCUMENTS

| | | | |
|---|---|---|---|
| 2,166,589 | 7/1939 | Harrington | 343/901 |
| 2,822,896 | 2/1958 | Schuster | 52/108 |
| 2,909,351 | 10/1959 | Pratt | 248/160 |
| 3,273,813 | 9/1966 | George | 242/54 A |
| 3,349,526 | 10/1967 | Schuster | 52/108 |
| 3,411,376 | 11/1968 | Weber et al. | 74/527 |
| 3,427,769 | 2/1969 | Star | 52/113 |
| 3,436,983 | 4/1969 | Krantz | 74/527 |
| 3,492,768 | 2/1970 | Schuster | 52/98 |
| 3,529,797 | 9/1970 | Street | 248/160 |
| 3,730,186 | 5/1973 | Edmunds, Jr. | 128/325 |
| 3,750,194 | 8/1973 | Summers | 128/1 R |
| 3,773,040 | 11/1973 | Gavrilovich | 128/79 |
| 3,832,996 | 9/1974 | Kalnberz | 128/79 |
| 3,851,430 | 12/1974 | Schuster | 52/108 |
| 3,853,122 | 12/1974 | Strauch et al. | 128/79 |
| 3,893,456 | 7/1975 | Small et al. | 128/79 |
| 3,954,102 | 5/1976 | Buuck | 128/79 |
| 3,963,037 | 6/1976 | Clark | 135/45 R |
| 3,987,789 | 10/1976 | Timm et al. | 128/79 |
| 3,991,752 | 11/1976 | Gerow | 128/79 |
| 4,009,711 | 3/1977 | Uson | 128/79 |
| 4,056,095 | 11/1977 | Rey et al. | 128/1 R |
| 4,066,073 | 1/1978 | Finney et al. | 128/79 |
| 4,151,840 | 5/1970 | Barrington | 128/79 |
| 4,151,841 | 5/1979 | Barrington | 128/79 |
| 4,176,411 | 12/1979 | Runge | 623/3 |
| 4,187,839 | 2/1980 | Nuwayser et al. | 128/79 |
| 4,201,202 | 5/1980 | Finney et al. | 128/79 |
| 4,204,530 | 5/1980 | Finney | 128/79 |
| 4,224,934 | 9/1980 | Scott et al. | 128/79 |
| 4,235,227 | 11/1980 | Yamanaka | 128/79 |
| 4,236,711 | 12/1980 | Klingbeil | 128/79 |
| 4,267,829 | 5/1981 | Barton et al. | 128/79 |
| 4,318,396 | 5/1982 | Finney | 128/79 |
| 4,335,714 | 6/1982 | Edgerton et al. | 128/79 |
| 4,353,360 | 10/1982 | Finney et al. | 128/79 |
| 4,369,771 | 1/1983 | Trick | 128/79 |
| 4,392,562 | 7/1983 | Burton et al. | 128/79 |
| 4,517,967 | 5/1985 | Timm et al. | 128/79 |
| 4,522,198 | 6/1985 | Timm et al. | 128/79 |
| 4,541,420 | 9/1985 | Timm et al. | 128/79 |
| 4,545,081 | 10/1985 | Nestor et al. | 128/79 |
| 4,594,997 | 6/1986 | Hakky | 128/79 |
| 4,594,998 | 6/1986 | Porter et al. | 128/79 |
| 4,619,251 | 10/1986 | Helms et al. | 128/79 |
| 4,628,912 | 12/1986 | Fischell | 128/79 |
| 4,665,902 | 5/1987 | Goff et al. | 128/79 |
| 4,693,719 | 9/1987 | Franko | 128/79 |
| 4,699,128 | 10/1987 | Hemmeter | 128/79 |
| 4,711,231 | 12/1987 | Finegold et al. | 128/79 |
| 4,718,411 | 1/1988 | Stewart | 128/79 |

FOREIGN PATENT DOCUMENTS

| | | |
|---|---|---|
| 714925 | 5/1946 | Fed. Rep. of Germany ........ 128/79 |
| 7805284 | 2/1978 | Fed. Rep. of Germany . |
| 2740263 | 3/1979 | Fed. Rep. of Germany ........ 128/79 |
| 3027681 | 11/1982 | Fed. Rep. of Germany ........ 128/79 |
| 3446157 | 7/1985 | Fed. Rep. of Germany . |
| 2151484 | 7/1985 | United Kingdom ................. 128/79 |

*Primary Examiner*—Gene Mancene
*Assistant Examiner*—Cary E. Stone
*Attorney, Agent, or Firm*—Merchant, Gould, Smith, Edell, Welter & Schmidt

[57] ABSTRACT

A penile prosthesis (20) including an articulated column (28) of segments (90) disposed intermediate of first and second end portions (24,26) of an elongated body (22) of the prosthesis (20). A tension assembly (31) cooperates with the segments (90) for causing frictional contact between the segments (90) at joints (96). The frictional contact resulting in a frictional force sufficient to provide the prosthesis (20) with positional stability throughout its range of motion, whereby the prosthesis will remain in any position where placed throughout its range of motion.

26 Claims, 5 Drawing Sheets

POSITION STABLE SEGMENTED COLUMN PENILE PROSTHESIS

This is a continuation of application Ser. No. 934,245, filed Nov. 21, 1986, abandoned.

BACKGROUND OF THE INVENTION

The present invention relates to a position stable segmented column penile prosthesis More particularly, the present invention relates to a position stable segmented column penile prosthesis wherein frictional force between adjacent segments retains the penile prosthesis in any position into which it is manipulated.

The causes of male impotence are many and varied. Various approaches to treating impotence have been developed in the past. Penile prostheses have been implanted within the penis to simulate an erectile state. There are several such prostheses known which use hydraulic or mechanical means of creating an artificial erection. The hydraulic devices provide an erect and a non-erect state, but have had reported problems of valve failure or fluid loss, each of which render the prosthesis unusable. An example of a hydraulic prosthesis is U.S. Pat. No. 3,954,102 to Buuck. The prosthesis is controlled by varying the amount of fluid in cylinders within the prosthesis by squeezing an elastomeric bulb through the patient's skin to transfer fluid from a reservoir into cylinders in the prosthesis. Because the reservoir and bulb are positioned outside of the prosthesis within the patient's body, the implantation procedure is quite complex and the extensive tubing required to interconnect the various portions of the system increase the possibility of failure. Other implantable prosthesis incorporating a reservoir pump and valving are shown in U.S. Pat. Nos. 4,369,771 and 4,353,360. As with the Buuck patent, these prostheses systems require pump and valving apparatus to be installed within the prosthesis and require the transfer of fluid from a reservoir into an inflatable portion for operation.

The mechanically operated prostheses are of basically three types. The first type is that of a solid rod of material, either flexible or inflexible. Although these types of prostheses provide adequate erection, in addition to other problems, there is patient discomfort due to the inability to conceal an erection. The second type of mechanical prosthesis device is a solid flexible rod having the added feature of a ductile metal core which provides adequate erection as well as the ability to bend the prosthesis into a concealable position An example of such a prosthesis device is U.S. Pat. No. 3,987,789 to Timm et al. In this patent, a prosthesis including an elongated malleable rod portion housed within a generally tubular physiologically inert plastic body is disclosed. The malleable rod portion enables the prosthesis to be conformed to a variety of shapes by bending or twisting. During intercourse, the prosthesis will maintain the penis in an erectile state and afterwards, the penis may be positioned and maintained by the user in a convenient, comfortable position. The prosthesis of Timm et al. depends upon its malleability to permit moving the prosthesis to a convenient, comfortable position or configuration. The flexibility of the prosthesis is not controllable by the patient. In addition to other problems, this prosthesis device has a limited life due to fatigue of the malleable material caused through normal use.

A third type of mechanical prosthesis device includes an articulated column of segments having a tensioning member and switch. This prosthesis device provides an erect condition or state by the tensioning member creating a force that pushes the segments of the articulated column together The force and the coefficient of friction of the segment material create a frictional force which facilitates maintaining the position of the segments relative to each other. A flaccid state or condition is created by activating a switch which reduces the tension of the tensioning member and so reduces the friction between the segments. With the friction reduced, the articulated column takes on a flaccid state and is readily capable of being concealed in a perfectly natural configuration. Examples of such a mechanical prosthesis device are commonly assigned Pat. Nos. 4,541,420; 4,522,198; 4,519,251, and 4,517,987. Although such a prosthesis device represents an improvement over the existing devices, the prosthesis device does require the presence of the switching element which increases the complexity of the prosthesis. Increasing the complexity of a device generally means an increase in cost and an increase in the probability of mechanical failure.

The present invention solves these and many other problems associated with currently available devices.

SUMMARY OF THE INVENTION

The present invention relates to a penile prosthesis having a range of motion between a concealed position and an erect position. The penile prosthesis includes an elongated body having a longitudinal axis and further having first and second end portions, the elongated body having an outer sheath of physiologically inert and pliable material. The elongated body of the penile prosthesis further includes an articulated column of segments disposed intermediate of the first and second end portions of the elongated body, adjacent ones of the segments cooperating to form joints therebetween. Friction causing means cooperates with the segments for causing frictional contact between the segments at the joints, the frictional contact resulting in a frictional force between the segments which resist relative movement between the segments, the frictional force being sufficient to provide the prosthesis with positional stability throughout its range of motion, whereby the prosthesis will remain in any position where placed throughout its range of motion.

The present invention provides a relatively uncomplicated penile prosthesis exhibiting positional stability about a range of motion which can be moved from an erect position to a concealed position by simply manually bending the prosthesis. Frictional force between adjacent segments of the articulated column enables the prosthesis to remain where positioned without requiring any external force.

Moreover, the present invention provides a penile prosthesis wherein the frictional force between adjacent segments is substantially increased when the segments are axially aligned and an axial force is applied forcing the ends of the prosthesis together, whereby the articulated column becomes more rigid, correspondingly causing the prosthesis to be more rigid.

It is an object of one embodiment of the present invention to provide a penile prosthesis having an articulated column of segments wherein a tension member is used to create the frictional force between adjacent ones of the segments. In one embodiment, the tension member will be a non-elastic cable member extending axially of the prosthesis. In yet other embodiments, an outer sheath will function as the tension member.

A further object of the invention is to provide a prosthesis which will not require a switch mechanism to alternately place the tension member in a tensioned and untensioned condition, thereby resulting in a less complex prosthesis structure.

In one embodiment of the invention, the frictional force is created by an interference fit between adjacent segments. A male end of each segment is captured by a female end of an adjacent segment such that the male end is biased (pulled) into the female end thereby creating the tension causing the frictional force between the adjacent segments.

In the preferred embodiment of the present invention, the frictional force between adjacent segments will remain substantially constant throughout the range of motion of the penile prosthesis and the surface area in frictional contact between adjacent ones of the segments will remain constant.

Yet another object of one embodiment of the present invention is to provide a penile prosthesis wherein the penile prosthesis has substantially the same degree of positional stability throughout its range of motion, whereby the force required to displace the prosthesis from one position to another throughout its range of motion is substantially constant.

In one embodiment of the present invention, the outer sheath will be made of elastomeric material so as to readily conform to the shape of the prosthesis. As discussed, in some embodiments where the tension member is a cable-like member, the elasticity of the outer sheath will have minimal or negligible affect on the frictional force between adjacent segments.

In another embodiment, the outer sheath will be comprised of non-elastomeric expanded polytetrafluoroethylene (PTFE) material which is axially compressed and then coated with elastomeric material such that the sheath takes on the properties of an elastomeric material. The PTFE material provides the sheath with strength and toughness characteristic of a non-elastomeric material. In addition, the PTFE material provides the sheath with a low coefficient of friction which allows the sheath to readily slide over the surface of the segments.

In one embodiment of the present invention, the tension member is interconnected at both ends to the end portions of the prosthesis by spring means suitably anchored in the end portions. The spring means assist in maintaining the tension member at a uniform tension and enable the articulated column to be bent such that the bend of the individual segments is exceeded. This is useful during the insertion process wherein a midsection insertion is typically made. While inserting the prosthesis, the doctor can bend the prosthesis roughly in half so as to facilitate insertion through the incision.

In some embodiments, the adjacent facing surfaces of the segments are roughened to increase the coefficient of friction between the surfaces and thus increase the frictional force for a given tension.

In yet another embodiment of the present invention, the prosthesis is longitudinally symmetrical such that the end portions thereof can be interchanged.

One embodiment of the invention includes removable tip portions utilizing a push-on interference attachment to the end portions of the prosthesis such that the tip portions can be readily removed and interchanged without requiring the use of set screws or the like.

These and various other advantages and features of novelty which characterize the invention are pointed out with particularity in the claims annexed hereto and forming a part hereof. However, for a better understanding of the invention, its advantages and objects obtained by its use, reference should be had to the drawings which form a further part hereof, and to the accompanying descriptive matter, in which there is illustrated and described a preferred embodiment of the invention.

BRIEF DESCRIPTION OF THE DRAWINGS

In the drawings, in which like reference numerals and letters indicate corresponding parts throughout the several views.

DETAILED DESCRIPTION OF A PREFERRED EMBODIMENT

Figure 1:
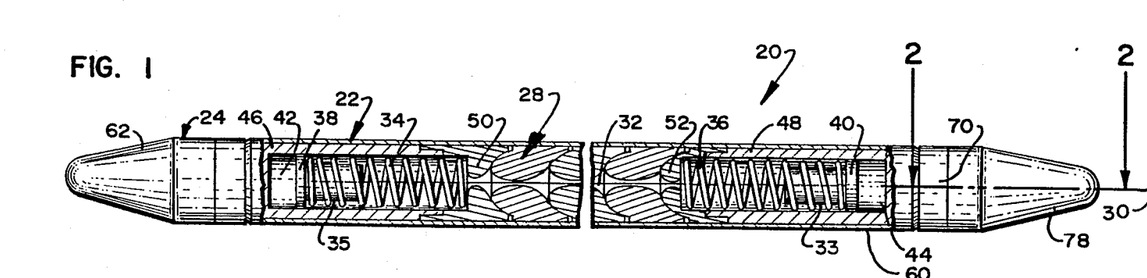
FIG. 1 is a longitudinal axial sectional view of a preferred embodiment of the present invention in an erect state.
Figure 2:
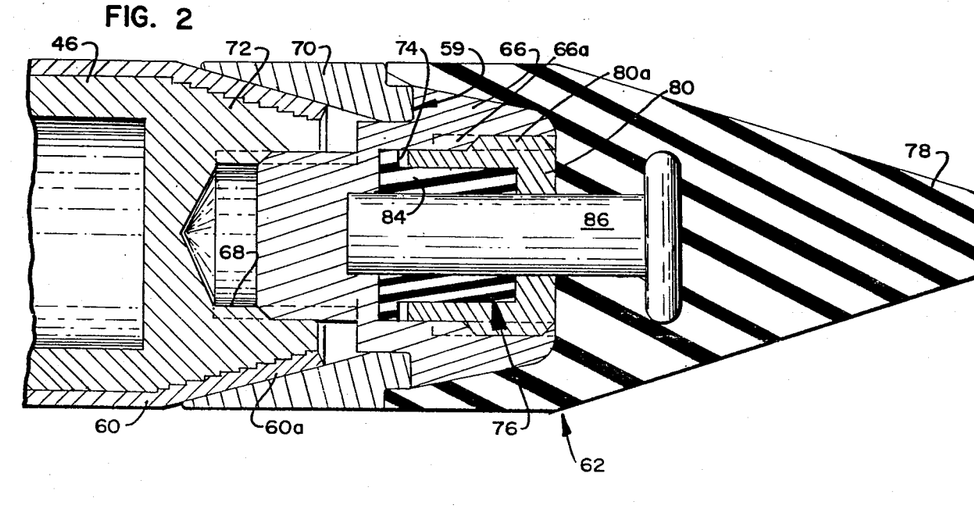
FIG. 2 is an enlarged sectional view as seen generally along line 2—2 of FIG. 1.

Referring now to the drawings, a preferred embodiment of a mechanical penile prosthesis in accordance with the principles of the present invention is illustrated in FIGS. 1-2, the penile prosthesis generally being referred to by the reference numeral 20. The prosthesis 20 is generally shown as having an elongated body 22 with first and second end portions 24,26. An elongated articulated column 28 is disposed between the first and second end portions 24,26 enabling pivotal or bending motion of the prosthesis 20 in all directions (360°) about a longitudinal axis 30 of the prosthesis 20. In the embodiment shown in FIG. 1, a tension assembly 31 forces the end portions 24,26 together to compress the articulated column 28. In the embodiment shown, the articulated column 28 is axially journaled about an axially extending, non-elastic, elongated tension member 32 which extends from a first spring member 34 to a second spring member 36. The tension member 32 is interconnected to the spring members 34,36 by retention members 27,29 including hollow cylindrical portions 33,35 and collar portions 38,40, the retention members 27,29 being crimped onto the tension member 32 at the cylindrical portions 33,35. The retention members 27,29 are slideably disposed in cavities 42,44, respectively, formed by housing portions 46,48, fixedly secured to housing portions 47,49, respectively. The spring members 34,36 are positioned over the cylindrical portions 33,35 so as to force against their respective collar portions 38,40 to place the tension member 32 under a predetermined tension which causes compression of the articulated column 28. The spring members 34,36 and their associated retention members 27,29 are placed in the cavities 42,44 during assembly prior to securing the housing portions 46,48 and 50,52 to one another.

The articulated column 28 and the tension assembly 31 are enclosed by a sheath 60 of physiologically inert and pliable material, such as silicone rubber, silicone coated polytetrafluoroethylene (PTFE), silicone tubing, or other physiologically inert elastomer which shields the prosthesis 20 from body tissue so as to prevent the growth of body tissue into the interworking, elements of the prosthesis which would otherwise affect operation of the working elements of the prosthesis and interfere with its proper function. In addition, such growth of body tissue into the prosthesis might also result in damage to the body tissue. In the preferred embodiment, the sheath 60 has elastomeric characteristics.

In one embodiment, the sheath is made from an elastomeric coated, non-elastomeric material 52. In particular, one embodiment of the invention uses expanded PTFE having expanded regions 51 with interstitial spaces 51a and fibrous material 51b and nonexpanded regions (nodes) 53. In this embodiment, the sheath 60 is formed as generally illustrated in FIGS. 8A–8D by placing the non-elastomeric expanded PTFE material 52 on a cylindrical mandrel 54, axially compressing the PTFE material 52, releasing the PTFE material 52, attaching the PTFE material 52 to the mandrel 54 with clamps or tie members 56, coating the non-elastomeric expanded PTFE material with elastomeric material 57 such as a silicone dispersion. In one embodiment, the PTFE material has a spacing between the nodes 53 of 22 microns. Non-elastomeric PTFE material 52 having a 12-millimeter outside diameter might be separated into lengths roughly twice that required of the sheath; e.g., 33 centimeters. The PTFE material 52 is then placed on the cylindrical mandrel 54, which might be made of a Teflon material and which further has an outside diameter substantially equal to the inside diameter of the PTFE material 52. In one embodiment, the PTFE material has an outside diameter of roughly 12 millimeters and is roughly 1 millimeter thick, so as to have an inside diameter of 10 millimeters. The PTFE material 52, while on the mandrel 54, is fully compressed and then released. It will be appreciated that when the non-elastomeric PTFE material 52 is released, it does not extend fully back to its original length. In the embodiment discussed above, the resultant length is roughly 15 centimeters. The ends of the PTFE material 52 are next clamped or tied onto the mandrel 54 and then the mandrel 54 is placed into a room temperature vulcanization (RTV) silicone dispersion. The silicone dispersion is diluted in xylene solvent at roughly a one to one ratio, or at a ratio so as to derive the desired viscosity necessary to provide the elastomeric coating with the proper thickness. In one embodiment, the silicone dispersion (dipping solution) has a viscosity of 25 seconds using a DUPONT ® No. M50 viscosity cup. While the mandrel 54 is submersed in the silicone dispersion, differential pressure is placed across the sheath wall so as to force the silicone dispersion into pores, also referred to as the interstitial spaces 51a, of the PTFE material 52. The differential pressure might be created in several ways, such as placing the silicone dispersion with the submerged PTFE material in a vacuum and then releasing the vacuum. The resultant atmospheric pressure will force the PTFE material into the interstitial spaces. Another approach is to use a hollow mandrel with openings therein. The mandrel is connected to a vacuum source to create a vacuum on the inside of the mandrel. The differential pressure applied will vary depending on the extent of adherence desired. The mandrel 54 and sheath are then removed from the dispersion so as to vulcanize the silicone whereby the silicone is mechanically bonded to the non-elastomeric PTFE material 52. During the vulcanization process, the sheath might be dried at room temperature for a short period of time and then inserted in an oven and heated to roughly 60° centigrade. Finally, the sheath might be removed and dried at room temperature for an extended period of time, such as three days. Upon completion of the vulcanization or curing process, the sheath is removed from the mandrel 54. It will be appreciated that the specific parameters given above are by way of example only and may be varied in keeping with the principles of the invention.

Figure 9A:
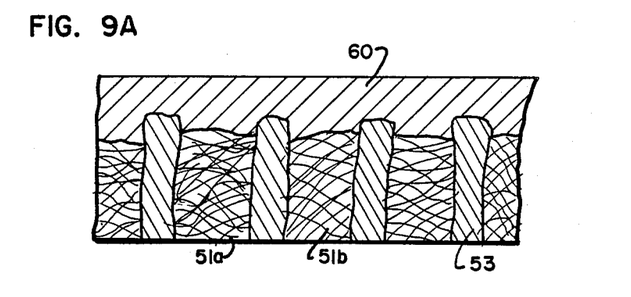
FIGS. 9A-9B are enlarged cross-sectional views of the sheath, made in accordance with the procedure illustrated in FIGS. 8A-8D, in stretched and relaxed states.
Figure 9B:
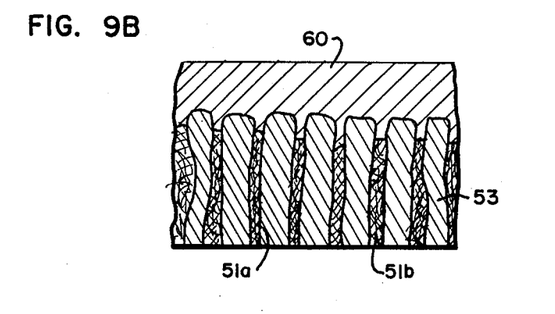

The end result of this process is a composite sheath material which has elastomeric characteristics, but also increased strength and toughness, as well as a low coefficient of friction and prevents tissue ingrowth. The resulting sheath has elastomeric characteristics due to the fact that the non-elastomeric PTFE material 52, after being fully compressed when placed on the mandrel 54, does not extend to its full length upon being released. As illustrated in FIGS. 9A–9B, the non-elastomeric PTFE material 52 can be stretched and have the elastomeric qualities of the silicone material without being damaged.

Interconnected to the first and second end portions 24,26 are tip portions 62,64, respectively. Referring now to FIG. 2, an embodiment of the end portions 24,26 and the tip portions 62,64 will be described in terms of the end portion 24 and the tip portion 62, the end portions 24,26 and the tip portions 62,64 being substantially identical in the preferred embodiment. The end portion 24 includes a retaining member 66 which is threaded into a threaded bore 68 of the housing member 46. A shoulder portion 65 of the retaining member 66, upon being threaded onto the housing member 46, engages and forces a wedge shaped retaining collar 70 onto a wedge shaped, barbed end 72 of the housing member 46 so as to wedge and securely retain in lace an end portion 60a of the outer sheath 60. The retaining member 66 defines a bore 74 receiving an attachment assembly 76 for attachment of a solid, flexible tip member 78. The attachment assembly 76 includes a compression body 80 and a deformable compression sleeve/collar arrangement 84. In the embodiment shown, the sleeve/collar arrangement 84 is of one piece, although it might be made of multiple pieces. The compression sleeve/collar arrangement 84 fits into an end of the compression body 80. The compression body 80 and the compression sleeve/collar arrangement 84 are all axially disposed about a cylindrical rod member 86 securely anchored in the tip 78. The attachment assembly 76 is screwed into the retaining member 66, the compression body 80 and the retaining member 66 including cooperating threads 66a and 80a, respectively. As the attachment assembly 76 is screwed into the retaining member 66, the compression sleeve/collar arrangement 84 is deformed so as to define an inside diameter substantially equal to or less than the outside diameter of the rod member 86. This deformation of the compression sleeve/collar arrangement 84 provides an interference (frictional) fit with the cylindrical rod member 86 such that the tip member 78 and its associated cylindrical rod member 86 is readily attached by simply pushing the member 86 into the bore 74. It is removed by simply pulling the member 86 from the bore 74. This provides the capability of readily interchanging the tip 78 such that any number of configurations and lengths of tips can be utilized on the end portions 24,26 depending on the specific requirements.

The force required to push or pull the rod member within the bore is adjusted by varying the deformation of the compression sleeve/collar arrangement 84. More deformation means greater force is required to push on the tip and pull off the tip.

An alternative to the attachment assembly has a compression sleeve 84 that extends beyond the compression body 80, requiring no compression collar, but acting in the same way otherwise.

Figure 3:
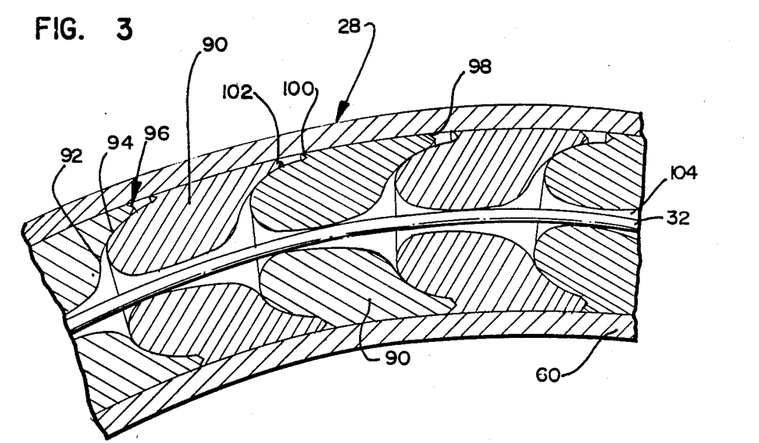
FIG. 3 is a partial enlarged longitudinal axial sectional view of an embodiment of an articulated column in accordance with the principles of the present invention.

Illustrated in FIG. 3 is an embodiment of an articulated column 28 in accordance with the principles of the present invention. As illustrated, the articulated column 28 includes radius segments 90 having a socket portion 91 defining a generally concave surface 92 proximate one end and a ball portion 93 defining a generally convex surface 94 proximate an opposite end. The facing concave and convex surfaces of adjacent ones of the radius segments 90 cooperate to form ball and socket joints 96 therebetween. (Moreover, the housing portions 50 and 52 include corresponding concave and convex surfaces for suitably abutting the end portions 24,26 with the articulated column 28.) In the preferred embodiment, a shoulder portion 98 is positioned about a periphery of each of the concave and convex surfaces 92,94, the facing shoulder portions of adjacent ones of the segments 90 cooperating to limit the amount of bending movement which occurs between adjacent ones of the segments. The amount of bending the articulated column is able to achieve is dependent on the amount each of the segments 90 is able to rotate on the adjacent segment 90. Accordingly, the segments 90 can be modified as desired to limit rotation of the segments 90 and thus bending of the articulated column 28. In the preferred embodiment, the prosthesis is able to rotate off its axis a minimum of 180° before becoming completely interlocked.

In the preferred embodiment, the contacting surface areas of adjacent segments 90 are substantially constant, the contacting surface area between adjacent segments remaining constant throughout the range of motion.

In the preferred embodiment shown, the shoulder portions 98 include cooperating indentations 100 and protuberances 102 which circumvent the concave and convex surfaces 92,94 of the segments 90 so as to prevent slippage between adjacent ones of the segments 90 and to provide a well-defined point for pivotal motion between individual ones of the segments 90. The segments 90 further define a bore 104 adapted for receipt of the tension member 32 such that the segments 90 are axially journaled about the tension member 32. Moreover, the segments 90 include radius surfaces so as to reduce wear on the tension member 32.

Figure 4:
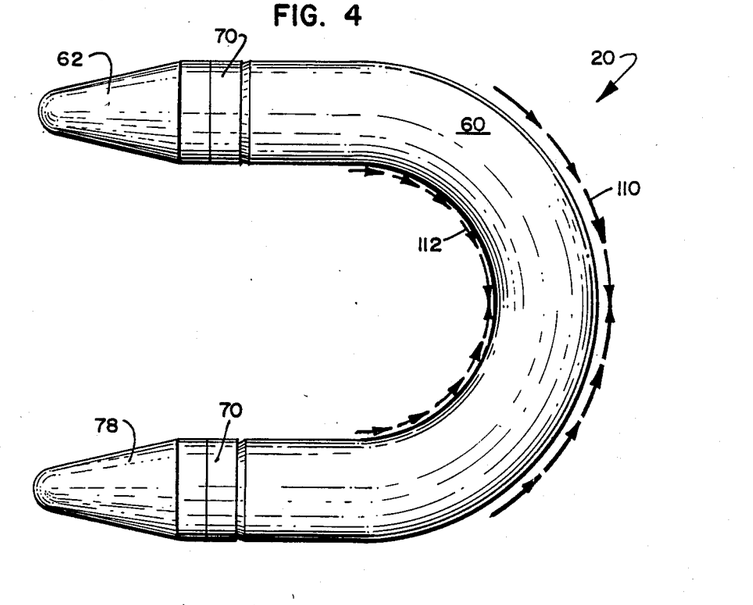
FIG. 4 is a diagrammatic view of an embodiment of the penile prosthesis in a concealed position illustrating the forces acting thereon.

The static frictional force (static frictional moment) between segments is roughly equivalent to the bending moment required to start rotating the device from the straight position. The bending moment of an item increases at a constant rate proportional to straightening forces which typically are present. In the present invention, the bending moment will preferably remain constant as the prosthesis is bent. As illustrated in FIG. 4, when the prosthesis 20 is bent to the concealed position, there are forces 110 and 112 which generally tend to straighten the prosthesis. However, the static frictional force (static frictional moment) created by the frictional contact between the segments 90 at the ball and socket joints 96 is sufficient to overcome the straightening forces (straightening moment) which tend to straighten the prosthesis 20. Accordingly, the prosthesis 20 will maintain any configuration wherein positioned.

The frictional force is affected by the radius of curvature (radius (r)) and the coefficient of friction (u) of the adjacent facing surfaces of the segments 90 and the tension (t) of the tension member 32. The frictional moment can be expressed as follows:

$$F = u \times r \times t$$

where
 F = frictional moment
 u = coefficient of friction
 r = radius of segments
 t = tension of tension member Accordingly, the frictional forces can be adjusted by varying the configuration and/or the coefficient of friction of the contacting surface areas of the segments and/or tension member tension. The straightening forces are affected by the outer sheath thickness, tension member diameter, and bending moment of the tension member. For example, the coefficient of friction might be increased by roughening the adjacent surfaces. In one embodiment, the segments might have adjacent contacting spherical surfaces with a radius of roughly 0.36 centimeters with a coefficient of static friction of 0.67, and a tension member tension of 4.0 pounds.

In a preferred embodiment, the frictional force between adjacent segments 90 remains substantially constant throughout the range of motion of the prosthesis. Indeed, in the preferred embodiment, the coefficient of friction, the radius (r), and the tension (t) remains constant. Moreover, in the preferred embodiment, the straightening force is minimized so a substantially constant or uniform straightening force is present throughout the range of movement of the prosthesis. Also, in a preferred embodiment, the contacting surface areas of adjacent segments 90 are substantially constant throughout the range of motion of the prosthesis.

Figure 5:
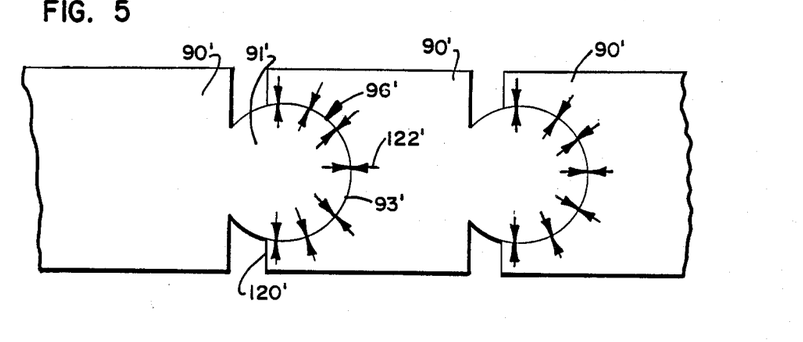
FIG. 5 is an enlarged diagrammatic view illustrating one embodiment of an articulated column of segments in accordance with the principles of the present invention.
Figure 6:
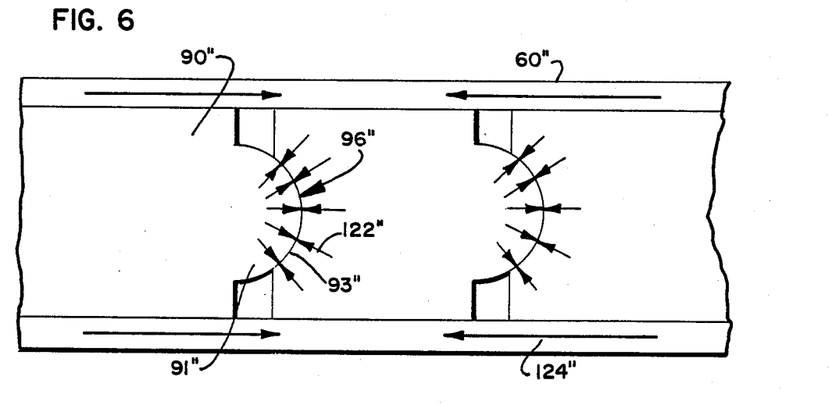
FIG. 6 is a view similar to FIG. 5 illustrating yet another embodiment of an articulated column of segments in accordance with the principles of the present invention.
Figure 7:
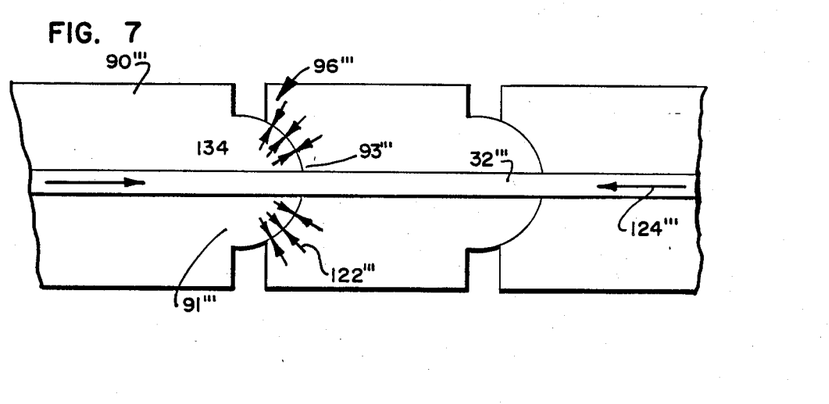
FIG. 7 is a view similar to FIG. 5 illustrating yet another embodiment of an articulated column of segments in accordance with the principles of the present invention.
Figure 8A:
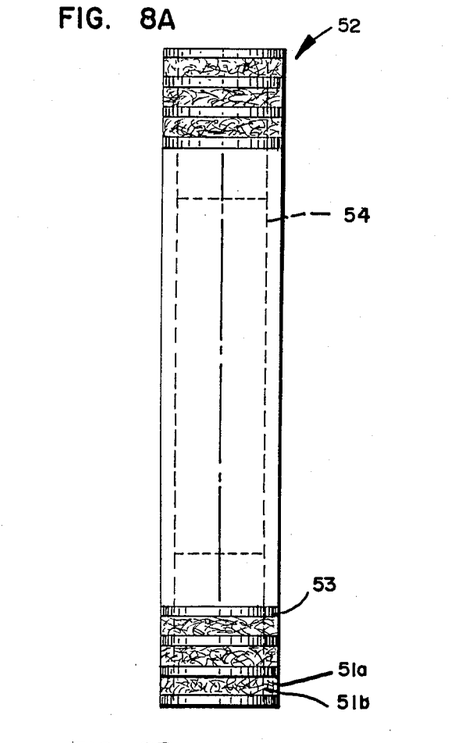
FIGS. 8A-8D are diagrammatic views illustrating various steps in making one embodiment of the outer sheath.
Figure 8B:
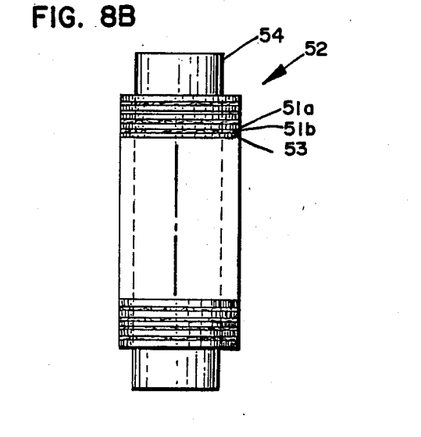
Figure 8C:
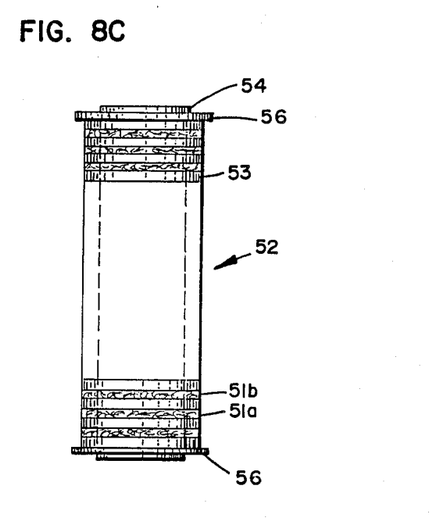
Figure 8D:
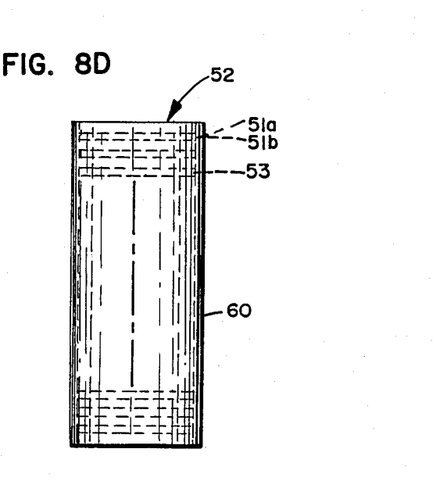

Illustrated in FIGS. 5-7 are three embodiments in accordance with the principles of the present invention, wherein frictional forces sufficient to create a positional stable prosthesis are provided. In FIG. 5, the segments 90' define ball and socket joints 96' wherein the socket portions 93' have an opening 120 with a diameter less than the ball portion 91' such that the ball and socket portions 91',93' cooperate to provide an interference fit between the segments 90' which are preferably made of a hard plastic material. The ball and socket portions 91',93' have the same diameters. The resultant frictional forces are generally represented by the arrows 122'.

Illustrated in FIG. 6 is an alternate embodiment wherein the segments 90" include ball and socket portions 91',93' wherein the external elastomeric sheath 60" functions as the tension member. The resultant frictional forces being illustrated by the arrows 122" and the compression force exerted by the sheath 60" being illustrated by the arrows 124". The tensioning force exerted by the sheath 60" must create frictional forces greater than the straightening forces. The sheath 60" tension can be adjusted by varying the pretension of the sheath 60". Illustrated in FIG. 7 is yet another embodiment of the present invention wherein the tension member comprises an elongated member 32'" about which the segments 90'" are axially journaled. The force exerted by the member being illustrated by the arrows 124'" and the frictional forces being illustrated by the arrows 122'".

As shown in FIGS. 5-7, the ball and socket joints 96',96", 96'" provide a joint with a constant surface area regardless of the orientation or configuration of the prosthesis 20.

The prosthesis 20 of the present invention is designed for implantation into the corpora cavernosa of the penis by conventional surgical procedures for treatment of erectile impotence. The prosthesis 20 is configured to generally match penile intracorporeal size and can be readily configured to do so so as to extend sufficiently proximally and distally when anchored within the penis in the body cavity so as to provide an erected penile state or condition and yet enabling concealment of the penis.

The present invention provides for volitional control of the penile erected and concealed positions. Moreover, the configuration of the present invention enables surgical implantation without regard for angular orientation and prevents malfunction if angular rotation is realized during use. In addition, the present invention is biologically compatible with the human body environment. Additionally, the penile prosthesis of the present invention may be readily positioned about a range of motion between a concealed position and an erect position simply by manual bending of the prosthesis 20.

The penile prosthesis 20 has a range of motion between a concealed position and an erect position as generally illustrated in FIG. 1 and a concealed position as generally illustrated in FIG. 4. The tension mechanism 31 and the articulated column 28 cooperate to provide the preferred embodiment of the present invention with position stable characteristics exhibiting positional stability throughout its range of motion; i.e., the prosthesis 20 will remain in any position where manually placed throughout its range of motion. Therefore, the state or condition of the prosthesis 20 is changed by simply bending the prosthesis to the desired configuration or position and does not require any switching action.

It is to be understood, however, that even though the above numerous characteristics and advantages of the invention have been set forth in the foregoing description, together with details of the structure and function of the invention, the disclosure is illustrative only, and changes may be made in detail, especially in matters of shape, size and arrangement of parts within the principles of the invention, to the full extent indicated by the broad general meaning of the terms in which the appended claims are expressed.

What is claimed is:

1. A penile prosthesis having a range of motion between a concealed position and an erect position, comprising:
    (a) an elongated body having a longitudinal axis and further having first and second end portions interconnected by an intermediate portion, the elongated body including an outer sheath of physiologically inert and pliable material;
    (b) the intermediate portion including an articulated column of segments disposed intermediate of the first and second end portions of the elongated body, adjacent ones of the segments cooperating to form joints therebetween; and
    (c) friction causing means cooperating with the segments for causing frictional contact between the segments at the joints, the frictional contact resulting in a frictional force sufficient to provide the prosthesis with positional stability throughout its range of motion, whereby the prosthesis will remain in any position where placed throughout its range of motion, the friction causing means including tension means for forcing adjacent ones of the segments into frictional contact with one another, the tension means including spring means disposed in at least one of the end portions, the intermediate portion having substantially uniform predetermined flexibility along its entire extent.

2. A penile prosthesis in accordance with claim 1, wherein the friction force is substantially constant throughout the range of motion of the prosthesis.

3. A penile prosthesis in accordance with claim 1, wherein the penile prosthesis has substantially the same degree of positional stability throughout its range of motion, whereby the force required to displace the prosthesis from one position to another throughout its range of motion is substantially constant.

4. A penile prosthesis in accordance with claim 1, further including removable tip portions interconnected to the end portions, whereby the overall length of the prosthesis can be varied.

5. A penile prosthesis in accordance with claim 4, wherein the end portions and tip portions include cooperating interference attachment means for removably attaching the tip portions to the end portions.

6. A penile prosthesis in accordance with claim 5, wherein the interference attachment means includes a cooperating rod and cylinder arrangement, rod member being insertable into a cylinder member so as to provide an interference fit.

7. A penile prosthesis in accordance with claim 1, wherein the tension means exerts a constant force for forcing adjacent ones of the segments into frictional contact with one another.

8. A penile prosthesis in accordance with claim 1, wherein the tension means includes an elongated tension member extending longitudinally of the elongated body.

9. A penile prosthesis in accordance with claim 8, wherein the tension member comprises an outer sheath.

10. A penile prosthesis in accordance with claim 8, wherein the tension member comprises an elongated cable member about which the segments are journaled.

11. A penile prosthesis in accordance with claim 10, wherein the elongated cable member is interconnected to the spring means at at least one of the elongated cable's ends.

12. A penile prosthesis in accordance with claim 8, wherein the tension member is interconnected proximate at least one end to force providing means for exerting a constant force on the tension member such that the tension member is placed under constant tension.

13. A penile prosthesis in accordance with claim 1, wherein adjacent ones of the segments include cooperating surface means providing an interference fit between the adjacent ones of the segments.

14. A penile prosthesis in accordance with claim 13, wherein the cooperating surface means include ball and socket elements, the ball element being insertable into the socket element, an entrance to the socket element having a lesser diameter than that of the ball element.

15. A penile prosthesis in accordance with claim 1, wherein the outer sheath is made of elastomeric material.

16. A penile prosthesis in accordance with claim 1, wherein the outer sheath is made of an expanded PTFE material which is compressed and released prior to being coated with an elastomeric material to provide an elastomeric sheath.

17. A penile prosthesis in accordance with claim 1, wherein the penile prosthesis is longitudinally symmetrical.

18. A penile prosthesis in accordance with claim 1, wherein the adjacent segments form ball and socket joints.

19. A penile prosthesis in accordance with claim 1, wherein the frictional force is increased upon axial application of a force when the segments are in axial alignment, whereby the prosthesis exhibits increased rigidity.

20. A penile prosthesis having a range of motion between a concealed position and an erect position, comprising:
 (a) an articulated column of segments located only in an intermediate portion of the prosthesis interconnecting opposing first and second end portions of the prosthesis; and
 (b) friction causing means for creating a frictional force between adjacent ones of the segments, the friction causing means cooperating with the articulated column for providing the prosthesis with positional stability and flexibility throughout its range of movement, the friction causing means including spring means disposed in at least one of the end portions, the end portions being substantially more resistant to flexing than the intermediate portion.

21. A penile prosthesis in accordance with claim 20, further including at least one replaceable tip portion, the tip portion and its corresponding end portion including cooperating rod and cylinder attachment means for removably attaching the tip portion to the corresponding end portion by insertion of a rod member into a cylinder member.

22. A method of making a penile prosthesis, comprising the steps of:
 (a) making an outer sheath, comprising the steps of:
  (i) sliding a non-elastomeric material onto a support member;
  (ii) applying a force to fully compress the non-elastomeric material in an axial direction;
  (iii) removing the force so as to release the non-elastomeric material;
  (iv) attaching the ends of the nonelastomeric material to the support member;
  (v) placing the support member and its associated non-elastomeric material into an elastomeric solution;
  (vi) placing a differential pressure across the non-elastomeric material so as to force the elastomeric solution into the non-elastomeric material;
  (vii) removing the support member and its associated non-elastomeric material from the elastomeric solution;
  (viii) drying the elastomeric solution coating the non-elastomeric material such that the elastomeric solution is solidified and a mechanical bond is formed between the elastomeric material and the nonelastomeric material; and
  (ix) removing the non-elastomeric material and its associated elastomeric material from the mandrel;
 (b) positioning an articulated column of segments about a tension member extending between first and second end portions;
 (c) enclosing the articulated column of segments with the outer sheath; and
 (d) attaching the outer sheath to the first and second end portions.

23. A method in accordance with claim 22, wherein the mandrel is placed into a room-temperature vulcanization (RTV) silicone dispersion.

24. A method in accordance with claim 22, wherein the non-elastomeric material includes expanded polytetrafluoroethylene (PTFE) material.

25. A method in accordance with claim 22, wherein a tip portion is removably attached to one of the first and second end portions by use of an interference fit.

26. A penile prosthesis comprising:
 (a) an elongated body including first and second end portions interconnected by an intermediate portion including an articulated column of segments, the intermediate portion having substantially uniform predetermined flexibility along its entire extent; and
 (b) friction causing means cooperating with the segments for causing frictional contact between the segments, the frictional contact resulting in a frictional force sufficient to provide the prosthesis with uniform positional stability throughout its range of motion, whereby the prosthesis will remain in any position where placed throughout its range of motion.

* * * * *